United States Patent
Park et al.

(10) Patent No.: US 9,227,997 B2
(45) Date of Patent: Jan. 5, 2016

(54) COMPOSITION FOR TREATING SEPSIS OR SEPTIC SHOCK COMPRISING THE PEPTIDE ORIGINATED FROM THE SMAD6

(71) Applicant: Medpacto, Inc., Suwon-si (KR)

(72) Inventors: Seok Hee Park, Suwon-si (KR); Youn Sook Lee, Suwon-si (KR); Yoe Sik Bae, Seongnam-si (KR); Seong-Jin Kim, Seoul (KR)

(73) Assignee: Medpacto, Inc., Suwon-si (KR)

( * ) Notice: Subject to any disclaimer, the term of this patent is extended or adjusted under 35 U.S.C. 154(b) by 0 days.

(21) Appl. No.: 13/730,423

(22) Filed: Dec. 28, 2012

(65) Prior Publication Data

US 2013/0172231 A1    Jul. 4, 2013

(30) Foreign Application Priority Data

Dec. 28, 2011 (KR) .................. 10-2011-0144262

(51) Int. Cl.
  C07K 7/08    (2006.01)
  A61K 38/10   (2006.01)
  C07K 1/107   (2006.01)
  A61K 47/48   (2006.01)

(52) U.S. Cl.
  CPC . C07K 7/08 (2013.01); A61K 38/10 (2013.01); A61K 47/48038 (2013.01); C07K 1/1077 (2013.01)

(58) Field of Classification Search
  CPC ........ C07K 7/08; C07K 1/1077; A61K 38/10; A61K 47/48038
  See application file for complete search history.

(56) References Cited

FOREIGN PATENT DOCUMENTS

WO    WO 9950296 A1 * 10/1999 ........... C07K 14/495

OTHER PUBLICATIONS

Hironori Tsujimoto, Role of Toll-Like Receptors in the Development of Sepsis, Shock, vol. 29, No. 3, pp. 315Y321, 2008.*
Djillali Annane, Corticosteroids for severe sepsis: an evidencebased guide for physicians, Annane Annals of Intensive Care Apr. 2011, 1:7, pp. 1-7.*
Drug Delivery and Targeting for Pharmacists and Pharmaceutical Scientists, Taylor & Francis Inc, Section 6.7.2, 2001.*
Sepsis Alliance (http://www.sepsisalliance.org/sepsis/treatment/, accessed on Oct. 22, 2014, published on-line Sep. 14, 2010.*
J. Mossague, et al. (2006). "Minireview: The logic of TGFβ signaling." *FEBS Letters.* vol. 580; pp. 2811-2820.
J. Mossague, et al. (2005). "Smad transcription factors." *Genes & Development.* vol. 19; pp. 2783-2810 (with cover page).
Y. Shi, et al. (Sep. 4, 1998). "Crystal Structure of a Smad MH1 Domain Bound to DNA: Insights on DNA Binding in TGF-β Signaling." *Cell.* vol. 94; pp. 585-594.
P. M. Siegel, et al. (Oct. 2003). "Reviews: Cystostatic and Apoptotic Actions of TGF-β in Homoestasis and Cancer." *Nature Reviews:Cancer.* vol. 3; pp. 807-820.
L. F. Weikert, et al. (Jun. 1996). "Pharmacotherapy of Sepsis." The Sepsis Syndrome. vol. 17. No. 2; pp. 289-305.
Lee, Youn Sook, "Studies about TGF-beta-mediated anti-inflammation mechanism by inhibitory Smads", Apr. 2010. Sungkyunkwan University Graduate school, Doctoral thesis.
Choi, Kyung-Chul, et al, "Smad6 negatively regulates interleukin 1-receptor Toll-like receptor signaling through direct interaction with the adaptor Pellino-1", Nature Immunology, Oct. 2006, vol. 7, No. 10, pp. 1057-1065.

* cited by examiner

*Primary Examiner* — James H Alstrum Acevedo
*Assistant Examiner* — Erinne Dabkowski
(74) *Attorney, Agent, or Firm* — NSIP Law

(57) ABSTRACT

Disclosed is a pharmaceutical composition comprising a Smad6-derived peptide as an active ingredient. Having ability to specifically bind to Pellino-1, the Smad6-derived peptide is effectively useful in the treatment of the sepsis mediated by excessively activated TLR. The peptide effectively reduces the expression of inflammatory cytokines, protects cells from sepsis-induced apoptosis, and exhibits high bacterial clearance in animal models of sepsis.

16 Claims, 8 Drawing Sheets

SEQUENCE LISTING

<160> NUMBER OF SEQ ID NOS: 16

<210> SEQ ID NO 1
<211> LENGTH: 20
<212> TYPE: PRT
<213> ORGANISM: Artificial Sequence
<220> FEATURE:
<223> OTHER INFORMATION: Smaducin-6

<400> SEQUENCE: 1

Gly Gly Arg Ala Leu Val Val Arg Lys Val Pro Pro Gly Tyr Ser Ile
 1               5                  10                  15

Lys Val Phe Asp
            20

<210> SEQ ID NO 2
<211> LENGTH: 18
<212> TYPE: DNA
<213> ORGANISM: Artificial Sequence
<220> FEATURE:
<223> OTHER INFORMATION: Forward primer of HA-Pellino-1 or HA-Pellino-1
      N

<400> SEQUENCE: 2
atgttttctc ctgatcaa                                                 18

<210> SEQ ID NO 3
<211> LENGTH: 18
<212> TYPE: DNA
<213> ORGANISM: Artificial Sequence
<220> FEATURE:
<223> OTHER INFORMATION: Reverse primer of HA-Pellino-1

<400> SEQUENCE: 3
ttagtctaga ggtccttg                                                 18

<210> SEQ ID NO 4
<211> LENGTH: 18
<212> TYPE: DNA
<213> ORGANISM: Artificial Sequence
<220> FEATURE:
<223> OTHER INFORMATION: Reverse primer of HA-Pellino-1 N

<400> SEQUENCE: 4
tctgcaggca aatcttga                                                 18

<210> SEQ ID NO 5
<211> LENGTH: 17
<212> TYPE: DNA
<213> ORGANISM: Artificial Sequence
<220> FEATURE:
<223> OTHER INFORMATION: Forward primer of Myc-Smad6 MH2, Myc-Smad6
      464R, Myc-Smad6 441R or Myc-Smad6 410R

<400> SEQUENCE: 5
tggtgcagcg tggcgta                                                  17

<210> SEQ ID NO 6
<211> LENGTH: 20
<212> TYPE: DNA
<213> ORGANISM: Artificial Sequence
<220> FEATURE:
<223> OTHER INFORMATION: Reverse primer of Myc-Smad6 MH2, Myc-Smad6
      346F, Myc-Smad6 371F or Myc-Smad6 385F

<400> SEQUENCE: 6
ctatctgtgg ttgttgagta                                                    20

<210> SEQ ID NO 7
<211> LENGTH: 18
<212> TYPE: DNA
<213> ORGANISM: Artificial Sequence
<220> FEATURE:
<223> OTHER INFORMATION: Forward primer of Myc-Smad6 346F

<400> SEQUENCE: 7
cgcctctatg cggtgtac                                                      18

<210> SEQ ID NO 8
<211> LENGTH: 18
<212> TYPE: DNA
<213> ORGANISM: Artificial Sequence
<220> FEATURE:
<223> OTHER INFORMATION: Forward primer of Myc-Smad6 371F

<400> SEQUENCE: 8
cagctcaacc tggagcag                                                      18

<210> SEQ ID NO 9
<211> LENGTH: 18
<212> TYPE: DNA
<213> ORGANISM: Artificial Sequence
<220> FEATURE:
<223> OTHER INFORMATION: Forward primer of Myc-Smad6 385F, Myc-Smad6
      385-441, Myc-Smad6 385-427, Myc-Smad6 385-418 or Myc-Smad6 385-410

<400> SEQUENCE: 9
cgcagcaaga tcggtttt                                                      18

<210> SEQ ID NO 10
<211> LENGTH: 18
<212> TYPE: DNA
<213> ORGANISM: Artificial Sequence
<220> FEATURE:
<223> OTHER INFORMATION: Reverse primer of Myc-Smad6 464R

<400> SEQUENCE: 10
gcgcacactg tgcgggtc                                                      18

<210> SEQ ID NO 11
<211> LENGTH: 18
<212> TYPE: DNA
<213> ORGANISM: Artificial Sequence
<220> FEATURE:
<223> OTHER INFORMATION: Reverse primer of Myc-Smad6 441R, Myc-Smad6
      385-441, Myc-Smad6 400-441 or Myc-Smad6 422-441

<400> SEQUENCE: 11
gtcgaacacc ttgatgga                                                      18

<210> SEQ ID NO 12
<211> LENGTH: 18
<212> TYPE: DNA
<213> ORGANISM: Artificial Sequence
<220> FEATURE:
<223> OTHER INFORMATION: Reverse primer of Myc-Smad6 410R, Myc-Smad6
      385-410 or Myc-Smad6 400-410

<400> SEQUENCE: 12
ggggtgctcg ccccggtt                                                      18

<210> SEQ ID NO 13

```
<211> LENGTH: 18
<212> TYPE: DNA
<213> ORGANISM: Artificial Sequence
<220> FEATURE:
<223> OTHER INFORMATION: Reverse primer of Myc-Smad6 385-427 or Myc-
      Smad6 400-427

<400> SEQUENCE: 13
gaccagggcg cggcctcc                                                        18

<210> SEQ ID NO 14
<211> LENGTH: 18
<212> TYPE: DNA
<213> ORGANISM: Artificial Sequence
<220> FEATURE:
<223> OTHER INFORMATION: Reverse primer of Myc-Smad6 385-418 or Myc-
      Smad6 400-418

<400> SEQUENCE: 14
cagcgtcggg gagttgac                                                        18

<210> SEQ ID NO 15
<211> LENGTH: 18
<212> TYPE: DNA
<213> ORGANISM: Artificial Sequence
<220> FEATURE:
<223> OTHER INFORMATION: Forward primer of Myc-Smad6 400-441, Myc-Smad6
      400-427, Myc-Smad6 400-418 or Myc-Smad6 400-410

<400> SEQUENCE: 15
ggcgtgtggg cctacaac                                                        18

<210> SEQ ID NO 16
<211> LENGTH: 18
<212> TYPE: DNA
<213> ORGANISM: Artificial Sequence
<220> FEATURE:
<223> OTHER INFORMATION: Forward primer of Myc-Smad6 422-441

<400> SEQUENCE: 16
gcgatcgcgg gcaggcgc                                                        18
```

COMPOSITION FOR TREATING SEPSIS OR SEPTIC SHOCK COMPRISING THE PEPTIDE ORIGINATED FROM THE SMAD6

CROSS REFERENCE TO RELATED APPLICATIONS

This application claims the benefit under 35 U.S.C. §119(a) of Korean Patent Application No. 10-2011-0144262 filed on Dec. 28, 2011, in the Korean Intellectual Property Office, the entire disclosure of which is incorporated herein by reference for all purposes.

BACKGROUND OF THE INVENTION

1. Field of the Invention

The present invention relates to a pharmaceutical composition for the therapy of sepsis or septic shock comprising a Smad6-derived peptide as an active ingredient, and a method for treating sepsis or septic shock using the same.

2. Description of the Related Art

Sepsis is a systemic inflammatory response syndrome that occurs in response to a pathogenic process in which, when Gram-negative bacteria infect the body, the toxin lipopolysaccharide (LPS), a cell wall constituent, excessively activates the immune system, with a side effect in severe cases of causing the body to go into shock. Sepsis is a serious disease, and a major cause of death among patients hospitalized with serious illnesses, with a mortality rate of 30%. In spite of great advances in medical technology, sepsis is often caused by infections which occur following surgical operations, and this happens all around the world. In addition, bacterial infection in people with weak immune systems, such as infants and the elderly, may be especially liable to develop sepsis. For example, neonatal sepsis is known to affect 3 in 1,000 mature infants, with a 3- to 4-fold increase in attack rate for immature infants. Upon the onset of sepsis, the treatment thereof generally rests on antibiotics. If bacteria grow too excessively due to the absence of proper treatment, or if bacteria are highly resistant to antibiotics, the sepsis cannot be effectively treated with antibiotics alone.

Like this, with the increasing advent of pathogens resistant to antibiotics, the treatment thereof has emerged as a very important and pressing task, but proper therapeutics have not yet been developed thus far (Weikert, L F Clin., Chest Med., 17, pp 289-305, 1996).

TGF-β (Transforming growth factor-β) is a cytokine that controls various physiological processes including cell growth, cell differentiation, apoptosis, cell migration, the production of extracellular matrix (ECM), vascularization, and embryogenesis in the body. The mature TGF-β protein dimerizes to produce a 25 KDa active molecule. TGF-β signaling begins with the binding of secreted, active TGF-β to a serine/threonine receptor kinase on the cell membrane. There are two classes of TGF-β receptors: type I and type II. The TGF-β binds to a constitutively active, type II receptor dimer, which phosphorylates and recruits a type I receptor dimer, forming a heterotetrameric complex with the ligand. In the TGF-β signaling pathway, Smad act as a transcription factor which transduces extracellular signals from TGF-β to the nucleus. When phosphorylated by a type II receptor, the type I receptor phosphorylates and activates Smad proteins, which, in turn, accumulate in the nucleus wherein they act in cooperation with other transcription factors to participate in the regulation of downstream gene expression (Masague J, Seoane J, Wotton D. Genes Dev 19:2783-2810, 2005).

In response to TGF-β, cells exhibit various activities which vary depending on the type of cells or the situation of stimuli, such as stimulated or inhibited growth, apoptosis, differentiation, etc. For example, TGF-β stimulates epithelial cells to actively proliferate, causing oncogenesis (Siegel P M, Massague J. Nat Rev Cancer 3: 807-821, 2003). Cytokines in the TGF-β family bind to various type I and type II receptors. Up to date, there are seven known type I receptors, called ALK (activin receptor-like kinase), and five type II receptors. TGF-β ligands utilize ALK5 and TR-2 receptors in most cells.

There are eight known Smad proteins, which can be divided into three classes: Receptor-activated Smads (R-Smad) which include Smad1, Smad2, Smad3, Smad5, and Smad8; Common mediator Smad (Co-Smad which includes only Smad4; and Inhibitory Smads (I-Smad) which include Smad6 and Smad7. On the whole, the TGF-β/Activin/Nodal group is mediated by Smad2 and Smad3 while the BMP/GDF/MIS group takes advantage of Smad1, Smad5, and Smad8 in the R-Smad. When bound to a ligand, the type I receptors directly phosphorylate the SSXS motif in the carboxyl tail of R-Smad, and the phosphorylated R-Smad, in turn, interacts with the Co-Smad, Smad4 and translocates into the nucleus where they bind to the Smad-binding element (SBE) on the DNA (Shi Y, Wang Y F, Jayaraman L, Yang H, Massague J, Pavletich N P. Cell 94: 585-594, 1998). Often, SBE acts as a binding site for other transcription factors so that the Smad regulates gene expression in cooperation with the other transcription factors. In contrast to R-Smad and Co-Smad, I-Smads (Smad6 and Samd7) have no carboxyl termini which can be phosphorylated by type I receptors, and downregulates the TGF-signaling. One of the most well known responses of cells to TGF-β is growth arrest. TGF-β induces cell growth arrest in epithelial cells, endothelial cells, blood cells, and nerve cells. Stimulation of TGF-β transduces the signals at any phase of the cell cycle, and also induces G1 arrest in the cell cycle (Massague J, Gomis R R. FEES Lett 580: 2811-2820, 2006). In epithelial cells, TGF-β stimulation induces the transcription of cyclin-dependent kinase inhibitors such as p21Cip1/WAF1 and p15lnk4b to activate anti-proliferative reactions, which leads to G1 arrest in the cell cycle. In addition, TGF-β inhibits the transcription of the pro-growth transcription factor c-Myc and the differentiation inhibitors ld1, ld2, and ld3. Also, TGF-β is known to induce various apoptotic reactions.

As reviewed above, TGF-β ligands and their signaling mediators, Smads, are not only involved in physiological activities such as cell growth, embryogenesis, and differentiation, but also play an important role in oncogenesis, fibrosis, and the onset and progression of various diseases. Factors and systems capable of controlling the signaling pathway, and detection methods thereof are now being actively studied.

However, any therapeutic effects that Smad6 in the TGF-β signaling pathway may have on sepsis or septic shock have yet to be discovered.

SUMMARY OF THE INVENTION

It is an object of the present invention to provide a pharmaceutical composition for the treatment of sepsis or septic shock, comprising a Smad6-derived peptide as an active ingredient, which is specifically therapeutic for the disease caused by the abnormal activation of Toll-like receptor 4 (hereinafter referred to as "TLR4"), as proven in experiments conducted with proteins involved in the TGF-β-induced signaling pathway, and a method for treating sepsis or septic shock using the same.

However, the objects to be achieved by the present invention are not limited to the above-mentioned, and those skilled in the art will appreciate that other objects could be apparently understood from the following description.

In accordance with an aspect thereof, the present invention provides a pharmaceutical composition for the treatment of sepsis or septic shock, comprising a Smad6-derived peptide as an active ingredient.

In one embodiment of the present invention, the Smad6-derived peptide has the amino acid sequence of SEQ ID NO: 1.

In another embodiment of the present invention, the onset and progression of sepsis is mediated by the activation of TLR4.

In a further embodiment of the present invention, the Smad6-derived peptide exerts a therapeutic effect on sepsis by inhibiting the production of inflammatory cytokines IL-6, TNF-α, IFN-γ and IL-1β, the activity of caspase-3, or the proliferation of TUNEL-positive cells.

In a still further embodiment of the present invention, the Smad6-derived peptide upregulates the expression of the chemokine receptor CXCR2 by inhibiting the expression of GRK2 that is inhibitory of the expression of the chemokine receptor CXCR2.

In still another embodiment of the present invention, the Smad6-derived peptide downregulates the IFN-β1-TRAIL pathway by inhibiting the formation of an IKKε/TBK1/Pellino-1 complex.

In yet another embodiment of the present invention, the Smad6-derived peptide binds to Pellino-1.

In accordance with another aspect thereof, the present invention provides a method for the treatment of sepsis or septic shock, comprising administering a pharmaceutical composition comprising a Smad6-derived peptide as an active ingredient, in a pharmaceutically effective amount to a subject in need thereof.

Having ability to specifically bind to Pellino-1, the Smad6-derived peptide composed of 20 amino acids in accordance with the present invention is effectively useful in the treatment of the infectious disease sepsis, particularly, the sepsis mediated by excessively activated TLR.

The Smad6-derived peptide consisting of 20 amino acids in accordance with the present invention was found to have therapeutic effects on sepsis or septic shock, as also seen on a molecular level in that the peptide was proven to bind specifically to Pellino-1, a TLR4 signaling mediator, thereby inhibiting the formation of the Pellino-1 complex responsible for downstream signaling.

BRIEF DESCRIPTION OF THE DRAWINGS

The above and other objects, features and other advantages of the present invention will be more clearly understood from the following detailed description taken in conjunction with the accompanying drawings, in which:

FIG. 3a is a schematic view of truncated mutants of the Smad6 MH2 domain, FIG. 3b shows co-immunoprecipitates and immunoblots obtained from HEK293 cells after transfection with plasmids carrying truncated mutants of Smad6 amino acid 422-441 (Myc-Smad6 (422-441)) or wild-type Smad6 MH2 domain (Myc-Smad6-MH2) plus an HA-tagged full length Pellino-1 plasmid, FIG. 3c shows co-immunoprecipitates and immunoblots obtained from HEK293 cells after transfection with a plasmid carrying Smad6 amino acid 422-441 (Myc-Smad6(422-441)) plus a plasmid carrying full length Flag-IRAK1, Flag-TRAF6, Flag-MyD88, or HA-Pellino-1, FIG. 3d is a graph showing TGF-β-induced luciferase activity in CMT-93 cells transformed with an SBE-Luc reporter plasmid plus an empty vector or a Myc-Smad6 (422-441) plasmid, FIG. 3e is a graph showing TGF-β-induced luciferase activity in CMT-93 cells transformed with a 5× NF-κB-Luc reporter plasmid plus an empty vector or a Myc-Smad6 (422-441) plasmid;

FIG. 4a is a graph showing IL-6 levels in RAW264.7 cells as measured by quantitative real-time RT-PCR after treatment with scrambled peptides (Pal-Scram; 100 nM) or Smaducin-6 and then with LPS, FIG. 4b is a graph showing luciferase activity in RAW264.7 cells transfected with a 5.times. NF-.kappa.B-Luc plasmid after treatment with scrambled peptides (Pal-Scram; 100 nM) or Smaducin-6 and then with LPS, FIG. 4c shows immunoblots obtained using respective antibodies to anti-I.kappa.B.alpha., anti-IKK.alpha., anti-phospho-IKK.alpha./.beta. in lysates of RAW264.7 cells that had been treated with scrambled peptides (Pal-Scram; 100 nM) or Smaducin-6 and then with LPS, with the use of .beta.-actin as a control, FIG. 4d shows co-immunoprecipitates obtained using an anti-IRK1 antibody in primary peritoneal macrophages extracted from mice treated with scrambled peptides (Pal-Scram; 100 nM) or Smaducin-6 and then with LPS, analyzing the formation of the endogenous IRK1-mediated signaling complex responsible for downstream TLR4 signaling, FIG. 4e shows co-immunoprecipitates obtained using an anti-RIP1 antibody in primary peritoneal macrophages extracted from mice treated with scrambled peptides (Pal-Scram; 100 nM) or Smaducin-6 and then with LPS, analyzing the formation of the endogenous RIP1-mediated signaling complex responsible for downstream TLR4 signaling, and FIG. 4f shows co-immunoprecipitates obtained using an anti-IKK.epsilon. antibody in primary peritoneal macrophages extracted from mice treated with scrambled peptides (Pal-Scram; 100 nM) or Smaducin-6 and then with LPS, analyzing the formation of the endogenous IKK.epsilon.-mediated signaling complex responsible for downstream TLR4 signaling;

FIG. 5a shows graphs of survival rates of mice with CLP-induced sepsis after subcutaneous injection of Smaducin-6 and scrambled peptides at doses of 8 mg/kg, 12 mg/kg, and 16 mg/kg, FIG. 5b shows graphs of survival rates of mice injected with Smaducin-6 (16 mg/kg) 2, 4 and 10 hrs after CLP induction, FIG. 5c shows microphotograph images of splenocytes stained with hematoxylin-eosin from BALB/c mice treated with 16 mg/kg scrambled peptides or Smaducin-6 after sepsis was induced by CLP, and FIG. 5d is a graph showing survival rates of BALB/c mice treated with 16 mg/kg Smaducin-6 or scrambled peptides after septic shock is induced by LPS;

FIGS. 6a to 6i show levels of cytokines in blood samples from mice subcutaneously injected twice with Smaducin-6 or scrambled peptides at 2 and 14 hrs after CLP induction, as analyzed by ELISA, the blood samples being taken 24 hrs after CLP induction, and FIG. 6j shows immunoblots for IL-6 expression in the spleen and the liver of the mice treated with scrambled peptides or Smaducin-6;

FIG. 7a is a graph showing cell counts in the peritoneal fluid taken from sepsis mice treated with scrambled peptides or Smaducin-6, FIG. 7b is a graph showing neutrophil counts in the peritoneal fluid taken from BALB/c mice with LPS-induced septic shock at 12 hrs after LPS injection, FIG. 7c is a graph showing expression levels of CXCR2 on the surface of human neutrophils treated for 2 hrs with 100 nM scrambled peptides or Smaducin-6 and then for 2 hrs with LPS, as analyzed by FACS, and FIG. 7d shows immunoblots for GRK2 expression in human neutrophils or RAW264.7 macrophages treated for 2 hrs with 100 nM scrambled peptides or Smaducin-6 and then for 2 hrs with LPS.

DESCRIPTION OF THE PREFERRED EMBODIMENTS

Figure 1:
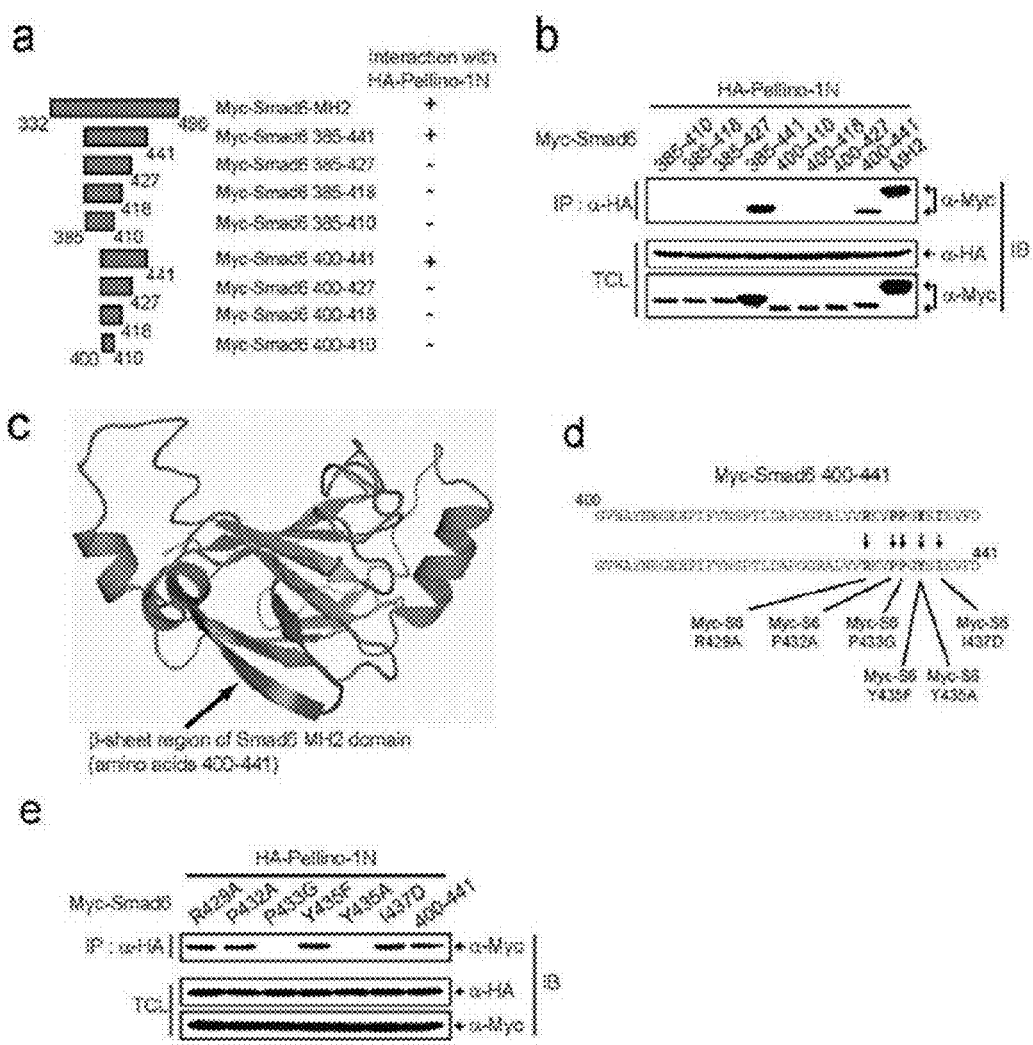
FIG. 1a describes the interaction of truncated mutants of Smad6 MH2 domain with Pellino-1N.
FIG. 1b shows immunoblots obtained from HEK293 cells transfected with plasmids carrying truncated mutants of Samd6 MH2, and an HA-tagged Pellino-1N plasmid.
FIG. 1c is an illustration of Smad6 MH2 domain as viewed by homology modeling.
FIG. 1d shows the amino acid sequence extending from amino acid position 400 to 441 of Smad6-derived peptide having the amino acid sequence of SEQ ID NO: 1, and a corresponding Myc-tagged Smad6 mutant (400-441)
FIG. 1e shows immunoblots obtained from HEK293 cells transfected with plasmids carrying site-directed mutants of Myc-tagged Smad6 (400-441), and an HA-tagged Pellino-1N plasmid.

The present invention addresses a pharmaceutical composition for the treatment of sepsis or septic shock, comprising a Smad6-derived peptide as an active ingredient.

The present inventors were the first in the world to find that the Smad6-derived peptide binds specifically to Pellino-1, which is involved in the TLR4-mediated signaling pathway and thus can be applied to the treatment of sepsis, because the onset and progression of sepsis is related with abnormal activation of TLR4.

TLR4 is a major receptor for LPS, a cell wall constituent of Gram-negative bacteria, functioning to mediate LPS signaling which leads to systemic inflammatory sepsis. TLR4 can be activated by endogenous ligands such as heparin sulfate and fibronectin, which are released from the lesion of tissue and cause the inflammatory response. Activation of TLR4 by LPS results in the oligomerizaiton of TLR4 oligomerization, with the subsequent recruitment of adaptor molecules. Generally, TLR4 signaling is dependent on MyD88 and TRIF (Toll/IL-1R domain containing adaptor-inducing IFN-β), which are major adaptor molecules interacting with the cytoplasmic portion of TLR4. Upon activation of TLR4 with LPS, MyD88 recruits IRAK-4 (IL-1R-associated kinase-4), thereby allowing the association of IRAK1. Together with TRAF 6 (TNFR-associated factor 6), these factors induce the activation of the IκB kinase (IKK) α/β/γ complex and MAPKs. TRIF is responsible for the activation of a signaling pathway independent on the MyD88-mediated signaling pathway, and interacts with TRAF 6 or TRAF 3 to activate RIP1, TBK 1 (TANK-binding kinase 1) and IKKε. Because activated TLR4 remarkably promotes the production of inflammatory proteins such as iNOS, COX-2, and TNF-α, abnormal activity of TLR4 is closely related to the onset of chronic inflammatory diseases as well as immunological diseases.

When its expression is upregulated by the anti-inflammatory cytokine TGF-β, Smad6 binds to Pellino-1, a novel factor involved in the TLR4-mediated signaling pathway, which leads to interruption of the TLR4-mediated signaling, with the subsequent inhibition of NF-κB activity essential for the expression of inflammatory genes. The inhibition of NF-κB activity induces the downregulation of inflammatory genes, thereby contributing to anti-inflammatory responses.

In the present invention, a minimum region of Smad6 capable of certainly binding to Pellino-1 was determined, and examined for ability to specifically suppress LPS-triggered NF-κB signaling. In one embodiment of the present invention, truncated mutants and site-directed mutants of Smad6 were constructed by mutation at small regions of Smad6 β-sheet, and subjected to co-immunoprecipitation with Pellino-1. As a result, a minimum region extending from amino acid 422 to 441 in the MH2 domain of Smad6 was found to bind only to Pellino-1, and did not bind to other proteins involved in the TLR4-mediated signaling. In addition, the expression of the minimum region (a.a. 422 to 441) of Smad6 which binds to Pellino-1 was observed to specifically suppress the NF-κB-mediated inflammatory signaling only (Examples 1 to 3).

In another embodiment, when the peptide consisting of amino acids at position 422 to 441 of Smad6 (Smaducin-6) was introduced into the inside of cells using a palmitic acid-induced-"flip-flop" process by which the peptide was exposed to the inside of the cell membrane, it was observed to suppress the LPS-triggered TLR4 signaling at a cellular level (Example 4).

In another embodiment of the present invention, Smaducin-6 was found to reduce the expression of inflammatory cytokines and to exhibit bacterial clearance in animal models of sepsis. In addition, experiments in sepsis mice exhibited that the peptide exerts a therapeutic effect on sepsis or septic shock through an anti-apoptotic mechanism (Examples 5 to 8).

From these results, the Smad6-derived peptide of the present invention is specific for sepsis or septic shock, and thus is expected to find applications in the therapy of sepsis or septic shock. Accordingly, the present invention envisages a pharmaceutical composition comprising an effective amount of a Smad6-derived peptide.

The pharmaceutical composition of the present invention may further a pharmaceutically acceptable carrier. Examples of the carrier include physiological saline, polyethylene glycol, ethanol, vegetable oil, and isopropyl myristate, but are not limited thereto.

In accordance with another aspect thereof, the present invention addresses a method for treating sepsis or septic shock, comprising administering a pharmaceutical composition in a therapeutically effective amount to a subject in need thereof, said pharmaceutical composition comprising a Smad6-derived peptide as an active ingredient. As used herein, the term "subject" is intended to refer to a target necessary for the treatment of a disease, and to encompass mammals including humans, and non-humans such as primates, mice, rats, dogs, cats, horses, and cows. The therapeutically effective amount of the pharmaceutical composition for a given patient may vary depending on various factors well known in the art, including the patient's weight, age, sex, state of health, and diet, the time of administration, the route of administration, the rate of excretion, and the severity of the disease.

The dose of a Smad6-derived peptide in the present invention may vary depending on various factors well known in the art, including a patient's condition, weight, the severity of the disease, the formulation of drug, the route of administration, and the duration of administration. Typically, the pharmaceutical composition of the present invention may be administered in a single dose or in multiple doses per day, at a daily dosage ranging from 0.001 to 100 mg/kg of weight and preferably from 0.01 to 30 g/kg of weight. The Smad6-derived peptide of the present invention may be present in an amount of from 0.0001 to 10 weight %, based on the total weight of the composition and preferably in an amount of from 0.001 to 1 weight %.

The pharmaceutical composition of the present invention may be administered to mammals such as rats, mice, cows, humans, etc. via various routes without limitations. For example, it may be administered orally or rectally or injected intravenously, intramuscularly, subcutaneously, intracervically or intra-cerebroventricularly.

A better understanding of the present invention may be obtained through the following examples which are set forth to illustrate, but are not to be construed as limiting the present invention.

EXAMPLE 1

Search for Small Regions of Smad6 MH2 Domain Responsible for Binding to Pellino-1

To examine a minimum region of Smad6 that binds certainly to Pellino-1, which specifically interrupts NF-κB (κB nuclear factor kappa B) signaling, mutants were constructed by consecutively truncating the Smad6 MH2 domain, and analyzed using a co-immunoprecipitation assay.

For this, HA-Pellino-1 was constructed by cloning a full-length cDNA of pellino-1 into the EcoRI/BamHI site of pSG5-2×HA. Plasmids carrying genes for different regions of Smad6 (Myc-Smad6 MH2, Myc-Smad6 346F, Myc-Smad6 371F, Myc-Smad6 385F, Myc-Smad6 464R, Myc-Smad6 441R, Myc-Smad6 410R, Myc-Smad6 385-441, Myc-Smad6 385-427, Myc-Smad6 385-418, Myc-Smad6 385-410, Myc-Smad6 400-441, Myc-Smad6 400-427, Myc-Smad6 400-418, Myc-Smad6 400-410, Myc-Smad6 422-441) were constructed by amplifying a full-length Smad6 cDNA by PCR and subcloning it into the BamHI/XhoI site of the pSC3+MT 6×Myc vector. Myc-Smad6 R429A, Myc-Smad6 P432A, Myc-Smad6 P433G, Myc-Smad6 Y435F, and Myc-Smad6 I437D were created using a QuikChange mutagenesis kit (Stratagene). All of the PCR products were identified by sequencing, and the primers used are summarized in Table 1, below.

TABLE 1

| Constructs | Direction | Sequence (5'-3') | SEQ ID NO: |
|---|---|---|---|
| HA-Pellino-1 | Forward | ATGTTTTCTCCTGATCAA | 2 |
|  | Reverse | TTAGTCTAGAGGTCCTTG | 3 |
| HA-Pellino-1 N | Forward | ATGTTTTCTCCTGATCAA | 2 |
|  | Reverse | TCTGCAGGCAAATCTTGA | 4 |
| Myc-Smad6 MH2 | Forward | TGGTGCAGCGTGGCGTA | 5 |
|  | Reverse | CTATCTGTGGTTGTTGAGTA | 6 |
| Myc-Smad6 346F | Forward | CGCCTCTATGCGGTGTAC | 7 |
|  | Reverse | CTATCTGTGGTTGTTGAGTA | 6 |
| Myc-Smad6 371F | Forward | CAGCTCAACCTGGAGCAG | 8 |
|  | Reverse | CTATCTGTGGTTGTTGAGTA | 6 |
| Myc-Smad6 385F | Forward | CGCAGCAAGATCGGTTTT | 9 |
|  | Reverse | CTATCTGTGGTTGTTGAGTA | 6 |
| Myc-Smad6 464R | Forward | TGGTGCAGCGTGGCGTA | 5 |
|  | Reverse | GCGCACACTGTGCGGGTC | 10 |
| Myc-Smad6 441R | Forward | TGGTGCAGCGTGGCGTA | 5 |
|  | Reverse | GTCGAACACCTTGATGGA | 11 |
| Myc-Smad6 410R | Forward | TGGTGCAGCGTGGCGTA | 5 |
|  | Reverse | GGGGTGCTCGCCCCGGTT | 12 |
| Myc-Smad6 385-441 | Forward | CGCAGCAAGATCGGTTTT | 9 |
|  | Reverse | GTCGAACACCTTGATGGA | 11 |
| Myc-Smad6 385-427 | Forward | CGCAGCAAGATCGGTTTT | 9 |
|  | Reverse | GACCAGGGCGCGGCCTCC | 13 |
| Myc-Smad6 385-418 | Forward | CGCAGCAAGATCGGTTTT | 9 |
|  | Reverse | CAGCGTCGGGGAGTTGAC | 14 |
| Myc-Smad6 385-410 | Forward | CGCAGCAAGATCGGTTTT | 9 |
|  | Reverse | GGGGTGCTCGCCCCGGTT | 12 |
| Myc-Smad6 400-441 | Forward | GGCGTGTGGGCCTACAAC | 15 |
|  | Reverse | GTCGAACACCTTGATGGA | 11 |
| Myc-Smad6 400-427 | Forward | GGCGTGTGGGCCTACAAC | 15 |
|  | Reverse | GACCAGGGCGCGGCCTCC | 13 |
| Myc-Smad6 400-418 | Forward | GGCGTGTGGGCCTACAAC | 15 |
|  | Reverse | CAGCGTCGGGGAGTTGAC | 14 |
| Myc-Smad6 400-410 | Forward | GGCGTGTGGGCCTACAAC | 15 |
|  | Reverse | GGGGTGCTCGCCCCGGTT | 12 |

TABLE 1-continued

| Constructs | Direction | Sequence (5'-3') | SEQ ID NO: |
|---|---|---|---|
| Myc-Smad6 422-441 | Forward | GCGATCGCGGGCAGGCGC | 16 |
| | Reverse | GTCGAACACCTTGATGGA | 11 |

A co-immunoprecipitation assay was carried out as follows. For use as antibodies in co-immunoprecipitation, mouse anti-HA (F-7), mouse anti-c-Myc (9E10), rabbit anti-IκBα (C-21), mouse anti-IRAK1 (F-4), and mouse anti-TRAF6 (D-10) were purchased from Santa Cruz Biotechnology (USA), the antibodies rabbit anti-Pellino-1 and rabbit anti-IRAK4 from Imgenex, the antibodies rabbit anti-Smad6, rabbit anti-MyD88 (D80F5), rabbit anti-IKKα, rabbit anti-phospho-IKKα/β, rabbit anti-RIP1 (D94C12), rabbit anti-IKKi (anti-IKKε; D61F9), rabbit anti-TBK1 (D1B4), rabbit anti-GRK2 from Cell Signaling, and the antibody anti-β-actin from Sigma. Cells were lysed in a lysis buffer (PBS containing 0.5% Triton X-100, 20 mM HEPES (pH 7.4), 150 mM NaCl, 12.5 mM β-glycerol phosphate, 1.5 mM $MgCl_2$, 10 mM NaF, 2 mM DTT, 1 mM $Na_3O_4V$, 2 mM EGTA, 1 mM PMSF and protease inhibitor mixture), and harvested by centrifuging 13,000 rpm for 10 min. For immunoprecipitation, the cell lysate were incubated at 4° C. for 12 hrs with protein-A agarose beads and the above-mentioned antibodies. Afterwards, the beads were washed three times with a lysis buffer, and treated with a 2× sample buffer to separate the co-immunoprecipitates therefrom. The co-immunoprecipitates were boiled, followed by SDS-PAGE.

Meanwhile, homology modeling of Smad6 domains was performed on SWISS-MODEL Workspace server60.

The results are given in FIG. 1. As can be seen in FIG. 1, a peptide region extending from amino acid 400 to 441 of Smad6 was identified to interact with the Pellino-1N domain (FIGS. 1a and 1b), and Smad6 mutants truncated at the amino acid positions 410 to 441 were observed to not bind the Pellino-1N domain. In addition, the structure of the small region extending amino acid 400 to 441 of the Smad6 MH2 domain was identified as a β-sheet as predicted by homology modeling (FIG. 1c).

These results demonstrate that the region extending from amino acid 410 to 441 of Smad6 is essential for the interaction with Pellino-1.

An examination was made to see whether the predicted structural factor plays an important role in binding to Pellino-1. In this regard, site-directed mutations were made in the small region, as shown in FIG. 1d, so as to detect the residues that contribute to the binding.

In the test for the binding of mutants of the Smad6 β-sheet region to Pellino-1, $Smad6^{P433G}$ and $Smad6^{Y435A}$ were observed not to interact with Pellino-1, respectively. As shown in FIG. 1e, the side chain-specific interaction mediated by Pro433 and Tyr435 was crucial for the binding of Smad6 to Pellino-1.

EXAMPLE 2

Effect of the Small Region of Smad6 MH2 Domain on NF-κB Signaling

Figure 2:
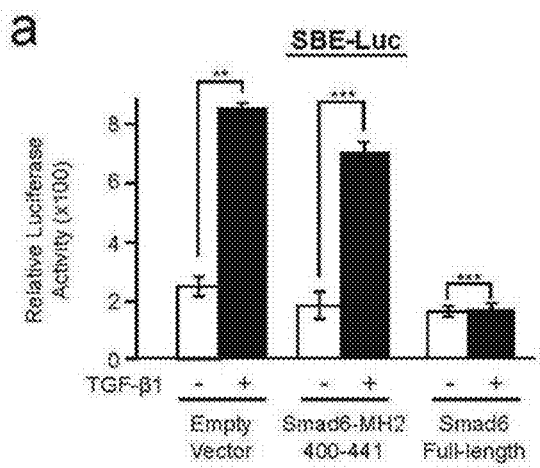
FIG. 2a is a graph showing results of the luciferase assay conducted with CMT-93 cells after transfection with SBE-Luc reporter plasmid plus an empty vector, a plasmid carrying Myc-Smad6 (400-441), or a plasmid carrying full-length Smad6.
FIG. 2b is a graph showing results of the luciferase assay conducted with CMT-93 cells after transfection with a 5×NF-κB-Luc reporter plasmid plus an empty vector, a plasmid carrying Myc-Smad6 (400-441), or a plasmid carrying full-length Smad6.
FIG. 2c shows immunoblots obtained using respective antibodies to IκBα, IKKα, and phospho-IKKα/β in CMT-93 cells transformed to stably express the peptide region 400-441 of Smad6 after treatment with lipopolysaccharides (hereinafter referred to as "LPS"), a cell wall constituent of Gram-negative bacteria.
Figure 2:
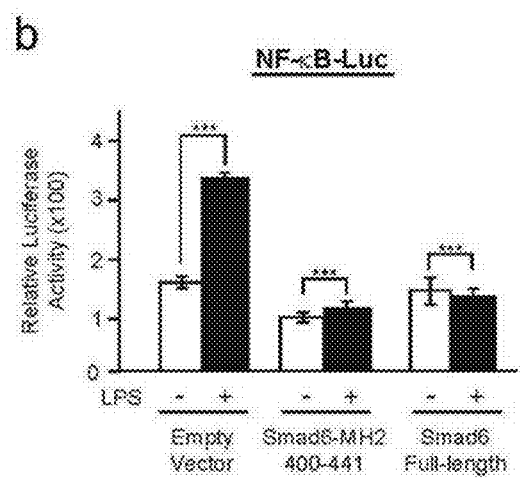
Figure 2:
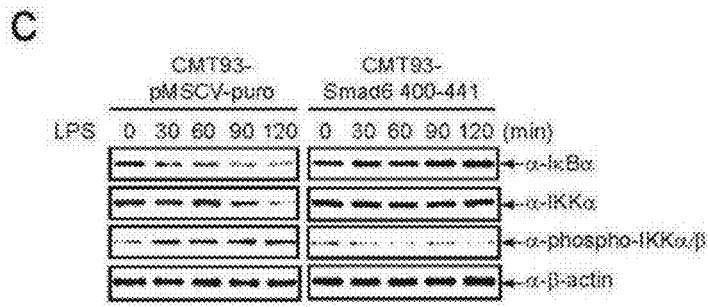

To examine whether the small region of Smad6 MH2 domain specifically suppresses LPS-induced NF-κB signaling, a 5× NF-κB-Luc reporter plasmid and an SBE (Smad binding element)-Luc reporter plasmid were separately transfected, together with a plasmid expressing a peptide from amino acid 400 to 441 of Smad6, into a CMT-93 epithelial cell line with the aid of Effectene (Qiagen). Following treatment with LPS (10 ng/ml) or TGF-β1 (5 ng/ml) for 2 hrs, the transfected cells were examined for luciferase activity. The results indicated that the small region of Smad6 MH2 domain, responsible for binding to Pellino-1, selectively suppressed NF-κB-mediated reporter activity (FIG. 2). All experiments were independently repeated three times, while a full-length Smad6 plasmid was used as a control.

As is apparent from the data of FIGS. 2a and 2b, both the NF-κB-mediated reporter activity and the TGF-β1-mediated reporter activity were suppressed with the expression of full-length Smad6. On the other hand, the expression of the β-sheet small region (amino acid 400 to 441) of Smad6 did not suppress the TGF-β1-mediated reporter activity, but selectively suppressed the NF-κB-mediated reporter activity only.

To confirm the specific inhibitory activity of the Smad6 β-sheet small region against NF-κB signaling, the epithelial cell line CMT-93, which is susceptible to both TGF-β1 and LPS, was transformed to stably express the Smad6 β-sheet region.

As can be seen in FIG. 2c, LPS-induced IκBα degradation was detected in the control CMT-93 transformed with an empty vector, but not in the CMT-93 cells expressing the Smad6 β-sheet small region.

From this result, it is understood that the small region (amino acid 400 to 441) of Smad6, responsible for interaction with Pellino-1, can be used to specifically regulate the inflammatory signaling pathway mediated by the transcription factor NF-κB.

EXAMPLE 3

Search for Minimum Region of Smad6 MH2 Domain Responsible for Interaction with Pellino-1

To characterize a minimum region of Smad6 MH2 domain, essential for binding to Pellino-1, the Smad6 MH2 domain was further fractionized. For this, plasmids carrying truncated mutants of the Smad6 β-sheet small region were constructed in the same manner as in Example 1, and subjected to a co-immunoprecipitation assay.

Figure 3:
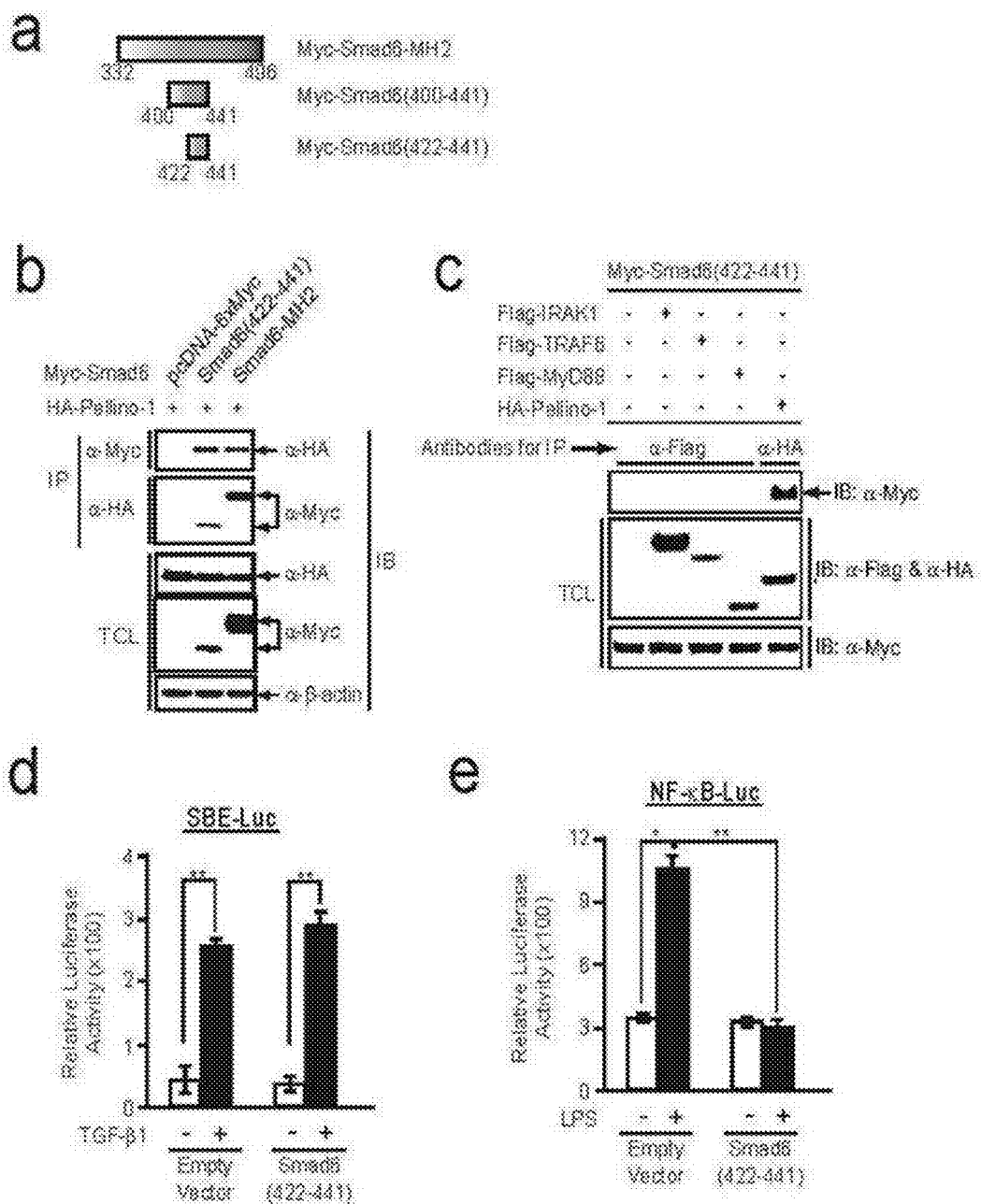
FIG. 3 shows suppressive effects of the minimum domain of Sma6 capable of interacting with Pellino-1 on NF-κB-mediated signaling.

The results are given in FIG. 3. As can be seen in FIGS. 3a and 3b, a peptide extending from amino acid 422 to 441 of Smad6 was sufficient and minimally required for binding to Pellino-1. In addition, the data of FIG. 3c indicates that the minimum region of Smad6 MH2 domain binds selectively to Pellino-1 only, but not to other proteins involved in the TLR4 signaling pathway. Further, as shown in FIGS. 3d and 3e, the expression of the minimum region (amino acid 422 to 441) of Smad6 resulted in specifically suppressing NF-κB-mediated reporter activity only, but did not suppressed the TGF-β-mediated reporter activity.

EXAMPLE 4

Effect of the Minimun Region (A.A. 422 to 441) of Smad6 on TLR4 Signaling

To examine whether the minimum region extending from a.a 422 to 441 of Smad6, essential for binding to Pellino-1, suppresses the LPS-induced TLR4 signaling cascade, palmitic acid was conjugated to the N-terminus of the peptide consisting of 20 amino acids of position 422 to 441 of Smad6 to construct a fatty acid peptide called Smaducin-6. For negative control, scrambled peptides (Pal-Scram) were constructed by conjugating palmitic acid to peptides synthesized with 20 randomly selected amino acids. Palmitic acid, a component of cell membranes, is characterized by a "flip-flop" process in which the fatty acid allows the peptide conjugated therewith to be exposed to the inside of the cell membrane. The palmitic acid-conjugated Smad6 amino acid 422-441 (Smaducin-6), and the negative control, that is, palmitic acid-conjugated Smad6 scrambled peptide were commercially synthesized and purified by Anygen. Smaducin-6 has the amino acid sequence given in Table 2, below.

TABLE 2

| Peptide | Amino Acid Sequence | SEQ ID NO: |
|---|---|---|
| Smaducin-6 | N terminal - GGRALVVRKVPPGYSIKVFD - C terminal | 1 |

Figure 4:
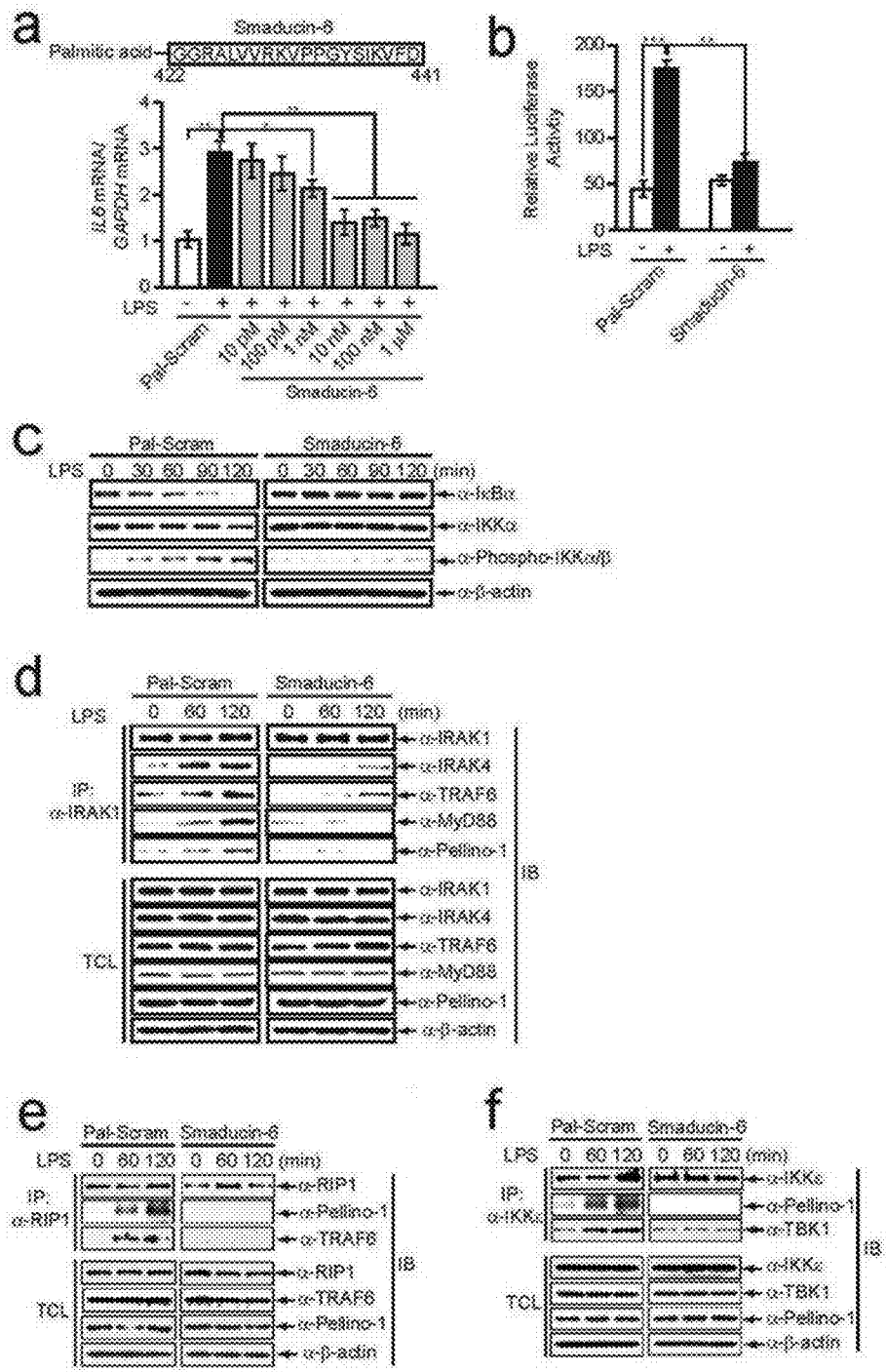
FIG. 4 shows suppressive effects of a peptide extending from amino acid 422 to 441 of Smad6-derived peptide having the amino acid sequence of SEQ ID NO: 1 (hereinafter referred to as "Smaducin-6"), conjugated with palmitic acid, on NF-.kappa.B-mediated signaling.

Smaducin-6 was assayed for ability to suppress LPS-induced TLR4 signaling, and the result is given in FIG. 4a. Pre-treatment of RAW264.7 mouse macrophages with Smaducin-6 reduced the expression of LPS-induced IL6 inflammatory gene in a dose-dependent manner.

In addition, when the RAW264.7 cells were stimulated with LPS, Smaducin-6 was observed to suppress NF-κB-mediated downstream signaling events including luciferase gene expression, IκBα degradation and IKKα/β phosphorylation (FIGS. 4b and 4c).

To examine whether Smaducin-6 interrupts the formation of the downstream signaling complex of TLR4, the cells were pre-treated with Smaducin-6 in the same manner as in Example 1, and analyzed for the LPS-induced formation of the signaling complex using a co-immunoprecipitation method. For control, the same experiment was conducted with scrambled peptides. The results are given in FIGS. 4d to 4f.

As is apparent from the data of FIGS. 4d to 4f, Smaducin-6 suppressed the LPS-induced formation of the IRAK1-, RIP1- or IKKε-mediated signaling complexes.

Consequently, Pellino-1 is involved in the expression of genes coding for inflammatory cytokines, and depletion of Pellino-1 leads to resistance to septic shock. Hence, the data showing that the Smaducin-6 peptide according to the present invention suppresses the formation of TLR4 signaling complexes by binding Pellino-1 suggest that in functioning to downregulate the abnormally increased activity of inflammatory cytokines, Smaducin-6, a novel peptide of the present invention, can be applied to the treatment of sepsis or septic shock.

EXAMPLE 5

Effect of Smaducin-6 on Sepsis in Animal Model

For use in assay for therapeutic effects of Smaducin-6 on sepsis, BALB/c mice were subjected to CLP (cecal ligation puncture) to prepare suitable animal models of clinical sepsis. Two hours after CLP operation on the mice, Smaducin-6 was subcutaneously injected at a dose of 8 mg/kg, 12 mg/kg, or 16 mg/kg to the mice, and then three more times at regular intervals of 12 hrs. In addition, an examination was made of the most effective time point of initial injection with Smaducin-6 after CLP operation. In this context, Smaducin-6 was initially injected at a dose of 16 mg/kg 2, 4, or 10 hrs after CLP operation, and then three more times at regular intervals of 12 hrs. Further, cells from various tissues of CLP mice were stained with hematoxylin-eosin to observe nucleus and cell morphology.

Figure 5:
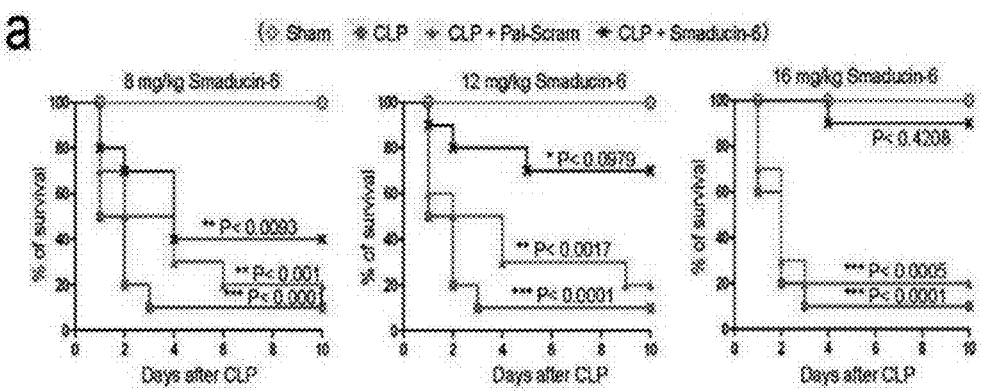
FIG. 5 shows the protective effect of Smaducin-6 in mice with sepsis induced by cecal-ligation-puncture (hereinafter referred to as "CLP")
Figure 5:
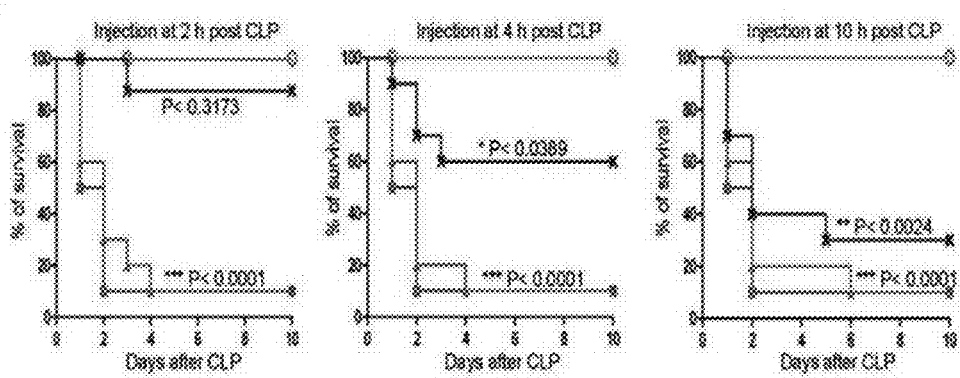
Figure 5:
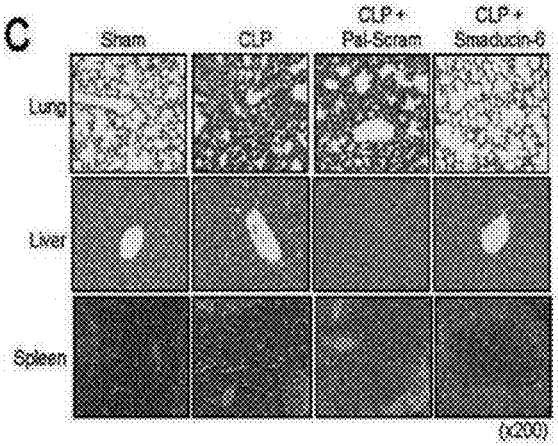
Figure 5:
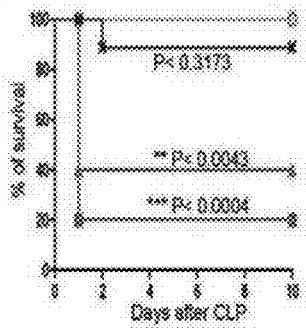

The results are given in FIG. 5. As can be seen in FIG. 5a, mice in which sepsis had been induced by CLP exhibited a mortality rate of 90% on day 2 or 3 after sepsis induction. In contrast to the control treated with the scrambled peptides, CLP mice survived at a rate of 90% when treated with 16 mg/kg Smaducin-6 and at a rate of 70% when treated with 12 mg/kg Smaducin-6. Hence, the peptide of the present invention significantly reduced the mortality rate.

As for the most effective time point of administration with 16 mg/kg Smaducin-6, as shown in FIG. 5b, the survival rate was 90% upon injection 2 hrs after CLP, and decreased to 60% upon injection 4 hrs after CLP. Cells and tissues of the lung, the liver, and the spleen excised from the CLP mice injected with Smaducin-6 at a dose of 16 mg/kg were found to be morphologically restored, compared to those from the control, as measured by hematoxilin-eosin staining assay (FIG. 5c).

Moreover, therapeutic effects of Smaducin-6 were examined in animal models of septic shock as well as CLP-induced sepsis. In this regard, LPS was intraperitoneally injected at a dose of 60 mg/kg into BALB/c mice, and from two hrs after LPS injection, Smaducin-6 was injected four times at regular intervals of 12 hrs into the mice. Survival rate measurements showed that Smaducin-6 is therapeutic for LPS-induced septic shock (FIG. 5d).

EXAMPLE 6

Effect of Smaducin-6 on Systemic Inflammatory Cytokines

In animal models of CLP-induced sepsis, Smaducin-6 was examined for ability to downregulate inflammatory cytokines. Blood samples were taken from each experimental group, and various cytokines and chemokines related with inflammatory responses were quantitatively measured. To the mice with CLP-induced sepsis, the peptide of the present invention was injected 2 and 14 hrs after CLP, and blood samples were collected 24 hrs after CLP. Levels of cytokines and chemokines in the blood samples were determined by ELISA using various antibodies according to the manufacturer's protocol. The antibodies used in this ELISA included mouse IL-6 (88-7064), IFN-γ (88-7314), TNF-α (88-7346), IL-4 (88-7044), IL-10 (88-7104), TGF-β1 (88-7344), IL-12 p70 (88-7121) and IL-17A (88-7371) ELISA Ready-SET-GO from eBioscience, Mouse IL-1β ELISA Set (559603) from BD Sciences, Mouse CXCL2/MIP-2 Immunoassay (MM200) from R&D Systems, and Mouse IFN-β ELISA Kit from PBL Biomedical Laboratories.

Treatment with Smaducin-6, as shown in FIGS. 6a to 6d, significantly reduced the levels of inflammatory cytokines such as IL-6, TNF-α, IFN-γ and IL-1β in the blood. In contrast, as shown in FIGS. 6e to 6i, there were no statistically significant changes in the levels of IL-4, IL-10, TGF-β1, IL-12 and IL-17A between groups treated with the scrambled peptide and the Smaducin-6 peptide.

Figure 6:
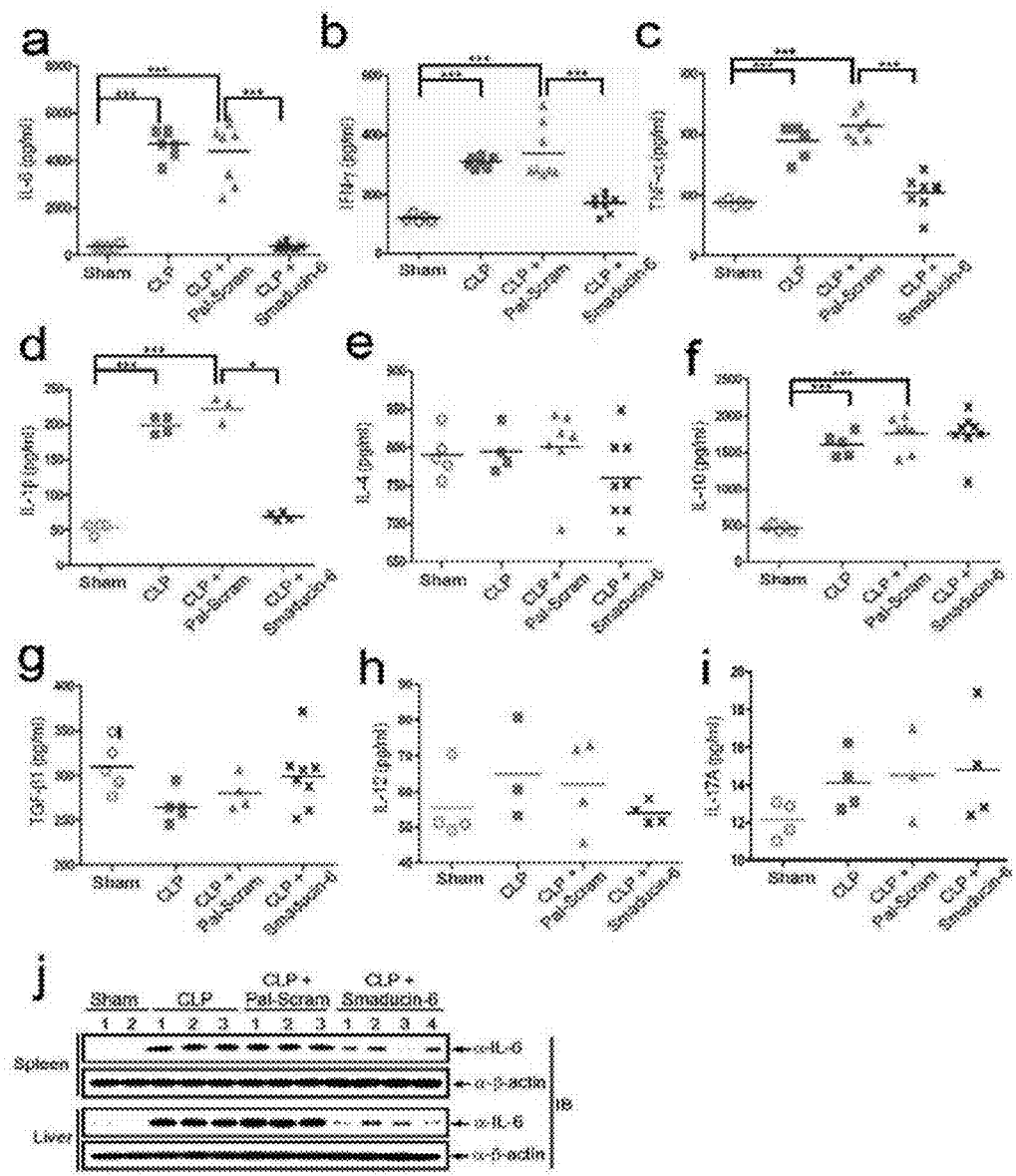
FIG. 6 shows the inhibitory effect of Smaducin-6 on inflammatory cytokines in mice with CLP-induced sepsis.

In addition, Smaducin-6 was found to reduce IL-6 expression in the spleen and the liver of the CLP mice, as measured by immunoblotting, indicating that Smaducin-6 is effective in the therapy for sepsis (FIG. 6j).

Taken together, the data obtained above demonstrate that the therapeutic effect of Smaducin-6 on sepsis is predominantly due to the reduction of systemic inflammation, but not due to the migration of immune response from TH1 to TH2.

EXAMPLE 7

Sterilizing Effect of Smaducin-6 through Neutrophil Migration

Figure 7:
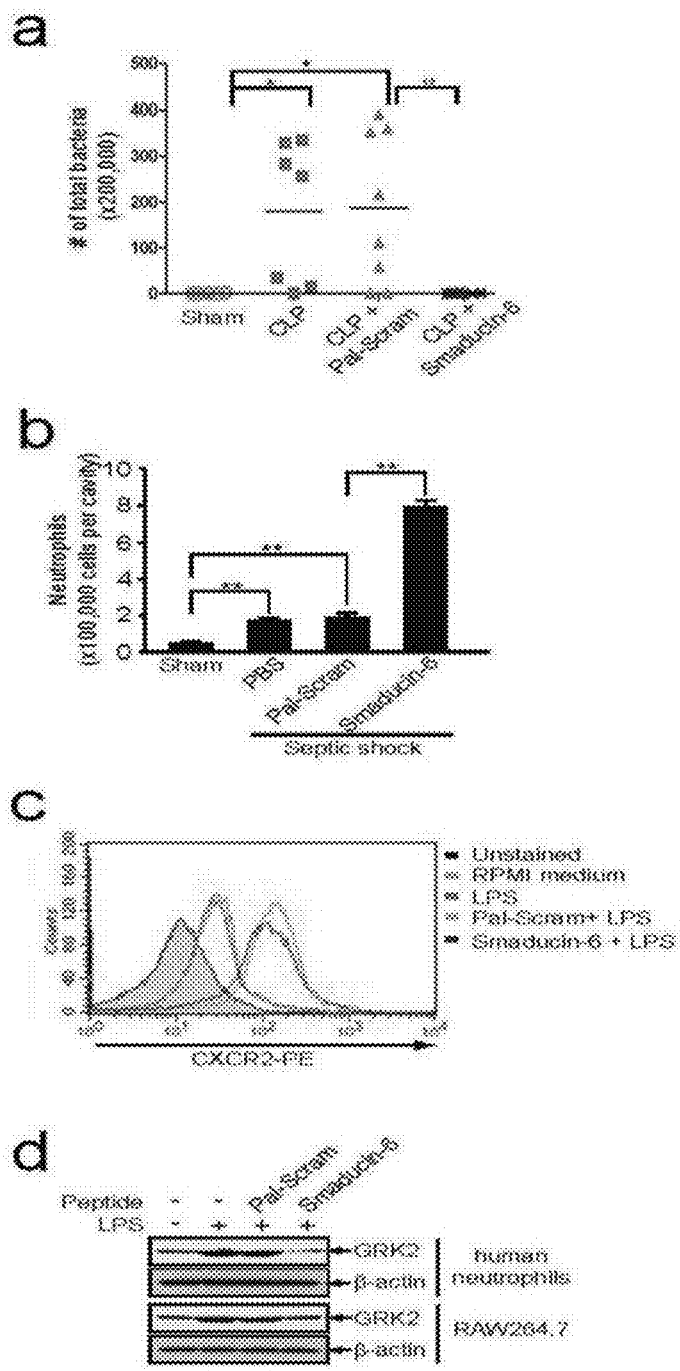
FIG. 7 shows the bacterial clearance effect of Smaducin-6 thorough neutrophils in mice with induced sepsis.

In mice with CLP-induced sepsis, the bacterial clearance of Smaducin-6 was examined. Smaducin-6 or the scrambled peptides were subcutaneously injected into CLP mice from which peritoneal fluid was then extracted from the mice, and bacteria in the fluid was counted. The result is given in FIG. 7a. As can be seen in this figure, the number of bacteria in the fluid from mice treated with Smaducin-6 was significantly lower than that of the control treated with the scrambled peptides. An examination was made to see whether this bacterial clearance of Smaducin-6 was attributed to the intraperitoneal migration of neutrophils. To this end, 2 and 14 hrs after induction of septic shock by injecting 60 mg/kg of LPS, Smaducin-6 or the scrambled peptides were injected into septic shock mice, and 24 hrs after the induction of septic shock, neutrophils were isolated from the peritoneal cavity using Histopaque-1077 (Sigma). Mouse neutrophils were counted using Trypan Blue (Sigma). As can be seen in FIG. 7b, the migration of neutrophils to the peritoneal cavity was increased in the septic shock mice treated with Smaducin-6, but was not observed in the control treated with the scrambled peptides.

To investigate the mechanism in which Smaducin-6 promotes peritoneal neutrophil migration, human neutrophils were treated for 2 hrs with 100 nM scrambled peptides or Smaducin-6 in advance of LPS treatment for 2 hrs. The expression of CXCR2, a chemokine receptor related with neutrophil migration, on the cell surface was analyzed using flow cytometry (FACS). Human neutrophils were isolated from normal human peripheral blood using Histopaque-1077 (Sigma) over a density gradient under the permission of the Institutional Animal Care and Use Committee of Ajou University, School of Medicine (Suwon, Korea).

The results are given in FIG. 7C. As can be seen in the graph of FIG. 7c, the expression of CXCR2 in human neutrophils was downregulated by LPS, whereas treatment with Smaducin-6 did not allow the downregulation of CXCR2 by LPS, but kept the expression of CXCR2 at a normal level.

To examine how Smaducin-6 interrupts with the LPS-induced downregulation of CXCR2, the levels of G-protein-coupled receptor kinase 2 (GRK2) in human neutrophils and RAW264.7 macrophages were measured. GRK2 is upregualted by LPS, which is known to suppress the expression of CXCR2.

As can be seen in FIG. 7d, LPS-induced GRK2 expression was downregualed in RAW264.7 cells and human neutrophils when they were treated with Smaducin-6.

These data imply that Smaducin-6 suppresses the expression of GRK2, which is upregulated by LPS, to protect the expression of CXCR2 from GRK2, thus promoting the peritoneal migration of neutrophils and macrophages.

EXAMPLE 8

Effect of Smaducin-6 on Apoptosis in Sepsis Mice

An examination was made to see whether Smaducin-6 suppresses apoptosis in mice with CLP-induced sepsis. The scrambled peptides or the Smaducin-6 peptide was injected into mice suffering from CLP-induced sepsis from which the spleen was then excised. Smaducin-6 was assayed for anti-apototic activity using the TUNEL method. The expression level of caspase-3, involved in apoptosis, was also determined using an immunohistochemical assay.

Figure 8:
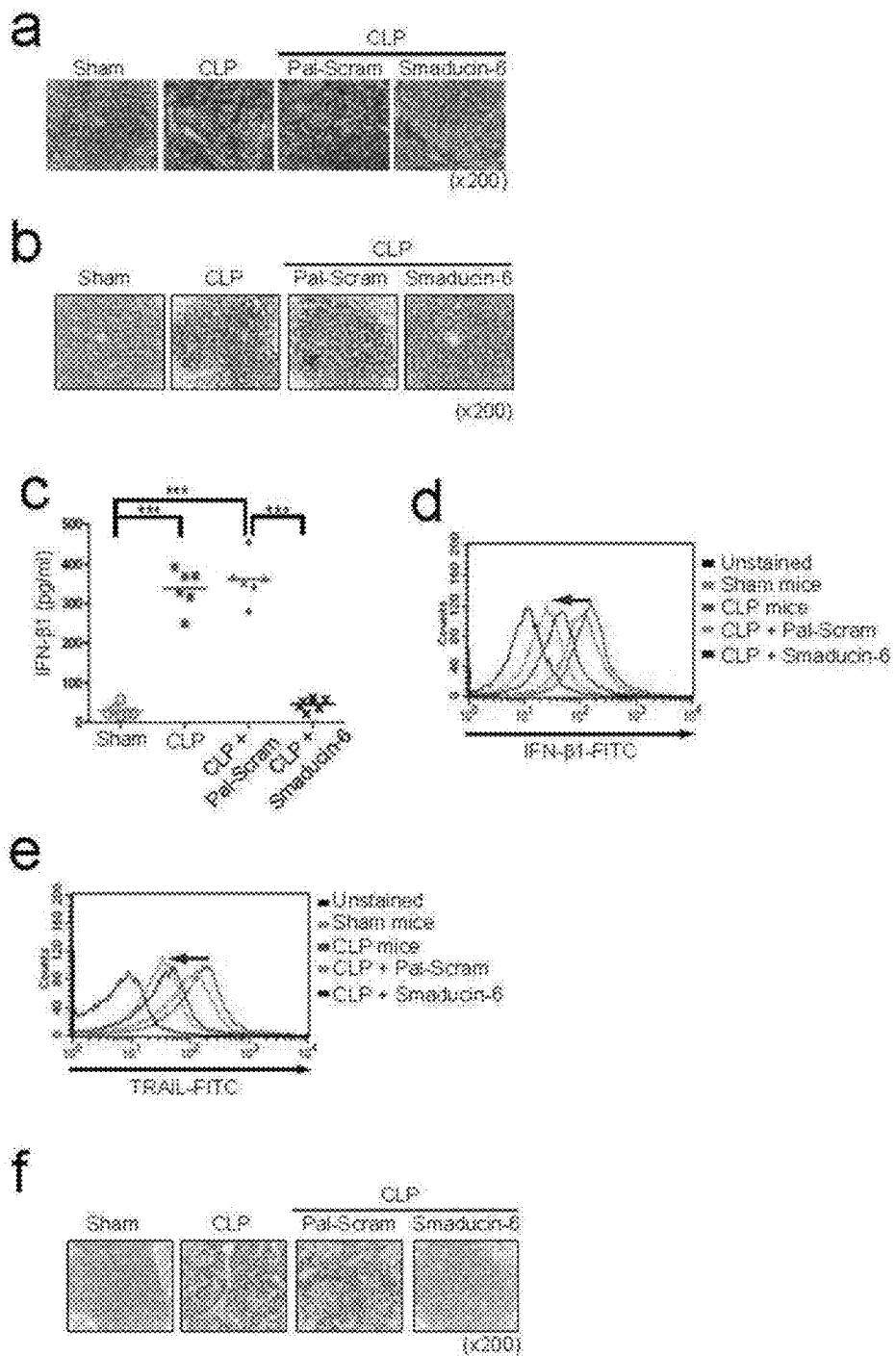
FIG. 8a shows microphotograph images of splenocytes of the mice subcutaneously injected twice with Smaducin-6 or scrambled peptides at 2 and 14 hrs after sepsis induction by CLP, as analyzed by the TUNEL assay, the splenocytes being taken from the mice at 24 hrs after sepsis induction.
FIG. 8b shows microphotograph images of splenocytes of the mice of FIG. 8a after immunohistochemistry for caspase-3 expression.
FIG. 8c is a graph showing levels of the IFN-β1 cytokine in peritoneal fluid from mice subcutaneously injected with Smaducin-6 or scrambled peptides at 2 and 14 hrs after sepsis induction by CLP, as analyzed by ELISA, the peritoneal fluid being taken 24 hrs after CLP induction.
FIG. 8d is a graph showing expression levels of IFN-β1 in splenocytes of mice subcutaneously injected with Smaducin-6 or scrambled peptides at 2 and 14 hrs after sepsis induction by CLP, as measured by FACS, the splenocytes being taken 24 hrs after sepsis induction.
FIG. 8e is a graph showing expression levels of TRAIL in splenocytes of mice subcutaneously injected with Smaducin-6 or scrambled peptides at 2 and 14 hrs after sepsis induction by CLP, as measured by FACS, the splenocytes being taken 24 hrs after sepsis induction.
FIG. 8f shows microphotograph images of splenocytes of the mice of FIG. 8a after immunohistochemistry for caspase-3 expression.

As a result, the level of TUNEL-positive cells was increased in the spleen from the sepsis mice treated with the scrambled peptides, but was significantly reduced in the spleen from the sepsis mice treated with the Smaducin-6 peptide (FIG. 8b).

To analysis the mechanism of the anti-apoptotic activity of Smaducin-6, an examination was made of the IFN-β1-induced TRAIL expression. In this regard, 2 and 14 hrs after CLP, the scrambled peptides or the Smaducin-6 peptide was injected to the mice, and the expression of IFN-β1 in the peritoneal fluid from the mice was analyzed using ELISA in the same manner as in Example 6. In splenocytes from each mouse group, the expression level of IFN-β1 was determined using flow cytometry (FACS). For flow cytometry, IFN-β1 was detected by FITC-conjugated anti-mouse IFN-β antibody (22400-3, interferon source), and stained before data analysis using CellQuest Pro software (BD Bioscience).

The results are given in FIGS. 8c and 8d. As can be seen in these graphs, the production of IFN-β1 was inhibited in the CLP mice treated with Smaducin-6.

Also, the effect of Smaducin-6 on the expression of TRAIL in mice with CLP-induced sepsis was examined. Splenocytes from the mice were subjected to flow cytometry and immunohistochemistry for TRAIL in the same manner as in Examples 8b and 8d. In this context, rabbit antibody TRAIL (C92B9, cell signaling), and FITC-conjugated goat antibody to mouse IgG (NOVUS) were used as a primary and a secondary antibody, respectively.

As can be seen in FIGS. 8e and 8f, TRAIL expression was reduced in the sepsis mice treated with Smaducin-6.

These data indicate that the Smaducin-6 peptide blocks sepsis-induced apoptosis, thus contributing to a reduction in the mortality of sepsis mice.

It is also understood that sepsis mice treated with Smaducin-6 was decreased in the activity of the IFN-β1-TRAIL pathway, which is incident with the data of Example 4, meaning that Smaducin-6 interrupts with the formation of the IKKε/TBK1/Pellino-1 signaling complex.

In the Examples, the survival study was analyzed using the log-rank test. The Mann-Whitney U test was used to compare counts of bacteria and neutrophils. For ELISA, the Dunnetts Multiple Comparison test was employed. Differences between test groups and controls were analyzed using the T-test (unpaired t test with Welch's correction), with significance of $P<0.05$.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A pharmaceutical composition for treatment of sepsis or septic shock, comprising a palmitic acid-conjugated Smad6-derived peptide consisting of the amino acid sequence represented by SEQ ID NO: 1, as an active ingredient.

2. The pharmaceutical composition of claim 1, wherein the sepsis is characterized by activation of Toll-like receptor 4 (TLR4).

3. The pharmaceutical composition of claim 1, wherein the papalmitic acid-conjugated Smad6-derived peptide exerts a therapeutic effect on sepsis by inhibiting production of inflammatory cytokines IL-6, TNF-α, IFN-γ and IL-1β, activity of caspase-3, or proliferation of TUNEL-positive cells.

4. The pharmaceutical composition of claim 1, wherein the palmitic acid-conjugated Smad6-derived peptide upregulates expression of a chemokine receptor CXCR2 by inhibiting the expression of GRK2 that is inhibitory of expression of the chemokine receptor CXCR2.

5. The pharmaceutical composition of claim 1, wherein the palmitic acid-conjugated Smad6-derived peptide downregulates an IFN-1β-TRAIL pathway by inhibiting formation of an IKKε/TBK1/Pellino-1 complex.

6. The pharmaceutical composition of claim 1, wherein the palmitic acid conjugated Smad6-derived peptide binds to Pellino-1.

7. A method for treatment of sepsis or septic shock, comprising administering a pharmaceutical composition in a pharmaceutically effective amount to a subject in need thereof, said pharmaceutical composition comprising a palmitic acid-conjugated Smad6-derived peptide consisting of the amino acid sequence of SEQ ID NO: 1, as an active ingredient.

8. The method of claim 7, wherein the sepsis is mediated by activation of Toll-like receptor 4 (TLR4).

9. The method of claim 7, wherein the effective amount of the palmitic acid-conjugated Smad6-derived peptide is an amount effective to exert a therapeutic effect on sepsis by inhibiting production of inflammatory cytokines IL-6, TNF-α, IFN-γ and IL-1β, activity of caspase-3, or proliferation of TUNEL-positive cells.

10. The method of claim 7, wherein the effective amount of the palmitic acid-conjugated Smad6-derived peptide is an amount effective to upregulate expression of a chemokine receptor CXCR2 by inhibiting the expression of GRK2 that is inhibitory of expression of the chemokine receptor CXCR2.

11. The method of claim 7, wherein the effective amount of the palmitic acid-conjugated Smad6-derived peptide is an amount effective to downregulate an IFN-β1-TRAIL pathway by inhibiting formation of an IKKε/TBK1/Pellino-1 complex.

12. The method of claim 7, wherein the effective amount of the palmitic acid-conjugated Smad6-derived peptide is an amount effective to bind to Pellino-1.

13. The method of claim 7, wherein the administering occurs within 10 hours of the onset of sepsis or septic shock.

14. The method of claim 13, wherein the administering occurs within 4 hours of the onset of sepsis or septic shock.

15. The method of claim 14, wherein the administering occurs within 2 hours of the onset of sepsis or septic shock.

16. The method of claim 7, wherein the administering comprises an initial administration followed by a subsequent administration about 12 hours after the initial administration.

* * * * *